(12) United States Patent
Sharma et al.

(10) Patent No.: US 6,713,504 B2
(45) Date of Patent: Mar. 30, 2004

(54) ANTIFUNGAL MOLECULE 2-(3,4-DIMETHYL-2,5-DIHYDRO-1H-PYRROL-2-YL)-1-METHYLETHYL PENTANOATE

(75) Inventors: Gainda Lal Sharma, Delhi (IN); Rajesh Dabur, Delhi (IN); Mohammad Ali, New Delhi (IN)

(73) Assignee: Council of Scientific & Industrial Research (IN)

( * ) Notice: Subject to any disclaimer, the term of this patent is extended or adjusted under 35 U.S.C. 154(b) by 6 days.

(21) Appl. No.: 10/100,055

(22) Filed: Mar. 19, 2002

(65) Prior Publication Data

US 2003/0181505 A1 Sep. 25, 2003

(51) Int. Cl.$^7$ .............................................. A61K 31/40
(52) U.S. Cl. ........................................ 514/428; 548/565
(58) Field of Search ........................... 548/565; 514/428

(56) References Cited

U.S. PATENT DOCUMENTS

2002/0197314 A1 * 12/2002 Rudnic et al. .............. 424/468

OTHER PUBLICATIONS

Saral, R., "Candida and Aspergillus Infections in Immunocompromised Patients: An Overview", Reviews of Infectious Diseases, 13, 487–492 (1991).
Koll, B.S., et al., "The Changing Epidemiology of Infections at Cancer Hospitals", Clinical Infection Diseases, 17 (Suppl. 2), S322–S328 (1993).
Denning, D.W., et al., "Antifungal and Surgical Treatment of Invasive Aspergillosis: Review of 2,121 Published Cases", Reviews of Infectious Diseases, 12, 6, 1147–1201 (1990).
Meyers, J.D., "Fungal Infections in Bone Marrow Transplant Patients", Seminars in Oncology, 17, 3, Suppl. 6, 10–13 (1990).
Allende, M.C., et al., "Dose–Dependent Antifungal Activity and Nephrotoxicity of Amphotericin B Colloidal Dispersion in Experimental Pulmonary Aspergillosis", Antimicrobial Agents and Chemotherapy, 38, 3, 518–522 (1994).
Stevens, MD, D.A., et al., "Analysis of Compassionate Use Itraconazole Therapy for Invasive Aspergillosis by the NIAID Mycoses Study Group Criteria", Arch Intern Med., 157, 1857–1862 (1997).
Gokhale, P.C., et al., "Development and Therapeutic Application of Liposomal Amphotericin B", Current Science, 65, 6, 448–454 (1993).
Denning, MB, MRCP, D.W., et al., "Intraconazole Therapy for Cryptococcal Meningitis and Cryptococcosis", Arch Intern Med., 149, 2301–2308 (1989).
Forthergill, A.W., et al., "In Vitro Susceptibility Testing of Yeasts", Clin. Microbiol. Procedure Handbook, 5.15.1–5.15.15 (1995).**

* cited by examiner

Primary Examiner—Joseph K. McKane
Assistant Examiner—Robert Shiao
(74) Attorney, Agent, or Firm—Piper Rudnick LLP; Steven B. Kelber

(57) ABSTRACT

The present invention relates to a novel antifungal molecule 2-(3,4-dimethyl-2,5-dihydro-1H-pyrrol-2-yl)-1-methylethyl pentanoate of formula (I) from a plant *Datura metel* a process for isolation and characterization of the molecule and a pharmaceutical composition essentially comprising the molecule as an antifungal agent.

20 Claims, 13 Drawing Sheets

TLC profiles of the active column
sub-fractions and purified compound.

1 2 3 4 5   Lane 1 & 2 Active column
sub fraction 10
Lane 3 & 4 Active column
sub-fraction 11
Lane 5 purified Compound ← Antifungal molecule Solvent System: Methanol: Chloroform: Formic acid (8.0: 2.0: 1.0)

Spray: Dragondroff's reagent

FIG.1

TLC profile of HPLC purified fraction.

A   B

A- Purified Compound

B- Column Sub-fraction

Inhibition of growth of *Aspergillus.fumigatus* by the disc diffusion method.

A-Test Compound (10 µg/disc)

B-Standard drug (2.5 µg/disc)

C- Solvent Control

ANTIFUNGAL MOLECULE 2-(3,4-DIMETHYL-2,5-DIHYDRO-1H-PYRROL-2-YL)-1-METHYLETHYL PENTANOATE

BACKGROUND OF THE INVENTION

1. Field of the Invention

The present invention relates to a novel antifungal molecule 2-(3,4-dimethyl-2,5-dihydro-1H-pyrrol-2-yl)-1'-methylethyl pentanoate of formula (I). It particularly relates to a novel antifungal lead molecule isolated from a plant *Datura metel*.

Formula (1)

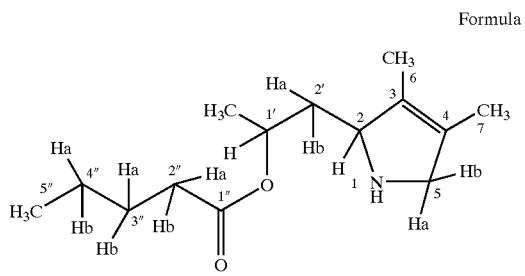

The main utility of the invention is to provide a new lead molecule for development of new drugs for treating diseases caused by pathogenic fungi.

2. Background of the Technology

The incidence and mortality due to mycotic infections has been observed to be on the rise in the past decade (Saral, R., 1991, Rev. Inf. Dis. 13, 487–492., Koll, B. S. and Brown, A. E. 1993, Clin. Inf. Dis. 17, S-322-S-326). Infections induced by these species are increasingly recognized as emerging threat to the public health. In immuno-compromised host, the infections by Aspergillus, Candida, Histoplasma etc. become invasive and disseminate from primary site of infection to other parts of the body including gut, kidney, brain etc. Invasive aspergillosis is reported to be associated with a mortality rate of 55% (Denning, D. W. and Stevens, D. A., 1990, Rev. Inf. Dis., 12, 1147–1201). Mortality due to Aspergillus infection in bone marrow transplant recipients was observed to be as high as 80% despite appropriate chemotherapy (Meyer, J. D., 1990, Semin. Oncol. 17 (suppl. 6), 10–13). Cerebral aspergillosis presents the symptoms of acute meningitis and is always fatal. Candida species are commensal organisms of human mucocutaneous surface. However, in immunocompromised host, Candida may progress to become opportunistic potential pathogen. It may be transmitted by contact to other immuno-compromised patients as a nosocomial pathogen.

It is, therefore, important to diagnose and treat these fungal infections at early stage to prevent irreversible damage. For the treatment of mycoses, several compounds belonging to azoles, polyenes and other groups of chemicals have been described in the literature. But all of these compounds have their own limitations.

Polyenes are among the oldest and most frequently prescribed antifungal agents. Amphotericin B is an important polyene drug which has been found to have a broad range activity against fungi, but its therapeutic doses are frequently associated with severe chills, fever, vomiting, life threatening hypotension and respiratory distress. Amphotericin B produces renal dysfunction (Allende, M. C., Lee, J. W., Francis, P., Garrett, K., Dollenberg, H., Berenguer, J., Lyman, C. A., Pizzo, P. A. and Walsh, T. J. 1994, Antimicrob. Agents and Chemother. 38, 518–522) and necessity of its intravenous administration is its major limitation (Stevens, D. A. and Lee, J. Y., 1997, Arch. Int. Med., 57, 1857–1862). In addition to its adverse effects, Amphotericin B resistance in fungal species has been reported (Gokhale, P. C., Kshirsagar, N. A. and Pandya, S. K., 1993, Current Science 65(6), 448–454, Forthergill, A. W. and McGough, D. A., 1995, Clin. Microbiol. Procedure Handbook, In Vitro susceptibility Testing of Yeast, 5.15.1–5.15.15).

Nystatin is another important drug, however, the development of resistance and its dose limited toxicity make this drug also less useful (Forthergill A. W. and McGough A. W., 1995, Clin. Microbiol. Procedure Handbook, In Vitro susceptibility Testing of Yeasts, 5.15.1–5.15.15).

New azole antifungals such as ketoconazole, fluconazole and itraconazole provided the hope that these compounds might be useful to prevent or treat fungal infections. However, their liver toxicity, hypoglycemic nature and development of resistant strains of fungi did not keep this hope alive for longer period (Denning, D. W. Tucker, R. M., Hanson, L. H., Hamilton, J. R. and Stevens, D. A., 1989, Arch. Int. Med., 149, 2301–2308). The azoles are reported to decrease the secretion of stomach acid and thereby reducing the absorption of drug itself and other important biomolecules. These effects may cause severe drop in body glucose to a level which may be life threatening. Resistance against the azole derivatives also has been reported in fungi (Forthergill A. W. and McGough A. W., 1995, Clin. Microbiol. Procedure Handbook, In Vitro susceptibility Testing of Yeasts, 5.15.1–5.15.14).

Currently available antifungal drugs are not sufficiently broad in their spectrum and not consistently effective against fungi including Aspergilli. These drugs are either toxic or immunosuppressive in nature. Further, the development of resistance in fungi to most of available drugs has also been reported.

It is evident from the above that need exists for development of new antifungal drugs which obviate the drawbacks listed above. The novelty of the present invention is to provide a process for isolation and characterization of a novel antifungal lead molecule from *Datura metel*, which is many fold less cytotoxic as compared to standard antifungal drug such as amphotericin B.

SUMMARY OF THE INVENTION

The main object of the present invention is to provide a novel antifungal lead compound 2-(3,4-dimethyl-2,5-dihydro-1H-pyrrol-2-yl)-1'-methylethyl pentanoate for developing new drugs against the pathogenic fungi.

Another object of the invention is to provide the process for isolation of the novel antifungal lead molecule 2-(3,4-dimethyl-2,5-dihydro-1H-pyrrol-2-yl)-1'-methylethyl pentanoate from a plant *Datura metel*.

Still another object of the present invention is to provide a method for testing the novel compound 2-(3,4-dimethyl-2,5-dihydro-1H-pyrrol-2-yl)-1'-methylethyl pentanoate as an antifungal agent.

Yet another object of the invention is to provide usage of the novel compound 2-(3,4-dimethyl-2,5-dihydro-1H-pyrrol-2-yl)-1'-methylethyl pentanoate as an antifungal agent.

Still yet another object is to provide a novel antifungal lead molecule 2-(3,4-dimethyl-2,5-dihydro-1H-pyrrol-2-yl)-1'-methylethyl pentanoate which is 57.8 times less cytotoxic than the standard antifungal drug such as Amphotericin B.

The present invention is directed to a novel antifungal compound 2-(3,4 dimethyl-2,5-dihydro-1H-pyrrole-2-yl)-1'-methylethyl pentanoate of the formula (1) as given below. The compound has antifungal properties and is several times less cytotoxic as compared to the standard antifungal drugs. This compound may be useful for controlling systemic and superficial fungal infections in humans with fewer toxic effects. This compound has been isolated from an easily available plant *Datura metel*.

BRIEF DESCRIPTION OF THE FIGURES

FIG. 1: Photograph of a plate showing TLC pattern of the active column sub-fractions and purified compound.

DESCRIPTION OF THE INVENTION

Accordingly the present invention provides a novel antifungal molecule 2-(3,4-dimethyl-2,5-dihydro-1H-pyrrol-2-yl)-1'-methylethyl pentanoate of formula 1

Formula 1

In an embodiment, the characterization of the active antifungal lead molecule is carried out by known analytical methods such as TLC, group specific chemical staining, UV, infra-red, mass and nuclear magnetic resonance spectroscopy and biological assays such as antimycotic assay and cytotoxicity assay.

Figure 7:
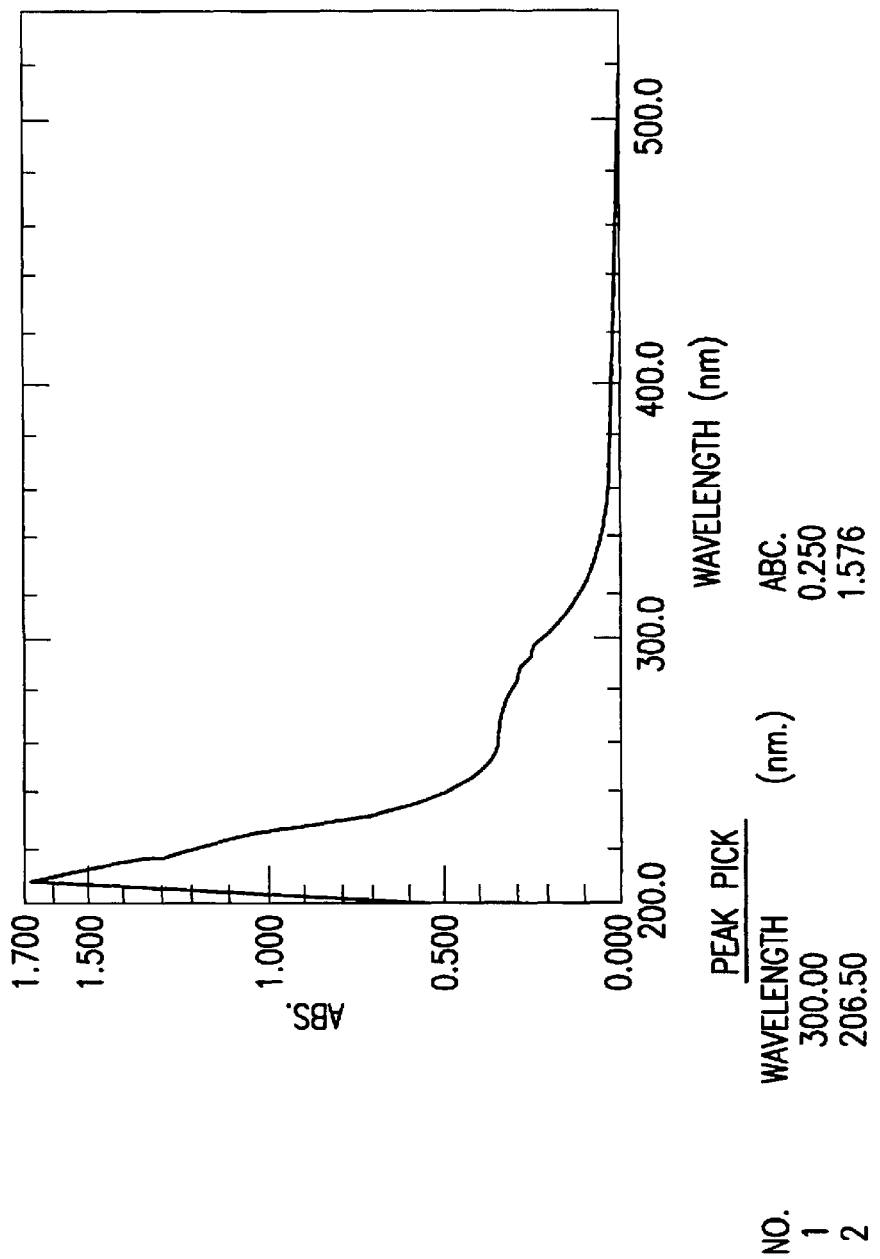
FIG. 7: UV spectrum of the compound.

In still another embodiment of the invention, the novel antifungal lead molecule 2-(3,4-dimethyl-2,5-dihydro-1H-pyrrol-2-yl)-1'-methylethyl pentanoate is a heterocyclic alkaloid as shown by group specific chemical staining using Dragendorff reagent and has following characteristics:

$R_f$ value of 0.22 on TLC (FIG. 3),

Absorption maixma at 300 nm and 206 nm in UV spectrum (FIG. 7)

Figure 8:
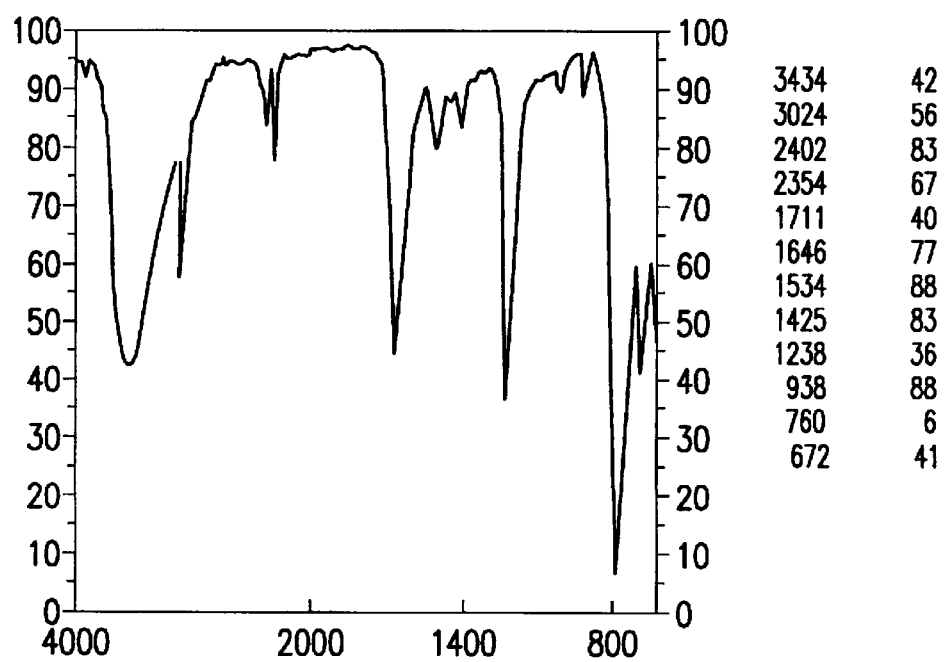
FIG. 8: IR spectrum of the compound.

IR $V_{Max}$: 3434 (NH), 3024, 1711 (ester), 1646 (C=C), 1524, 1426,1230, 938, 760 cm$^{-1}$ (FIG. 8).

Figure 9:
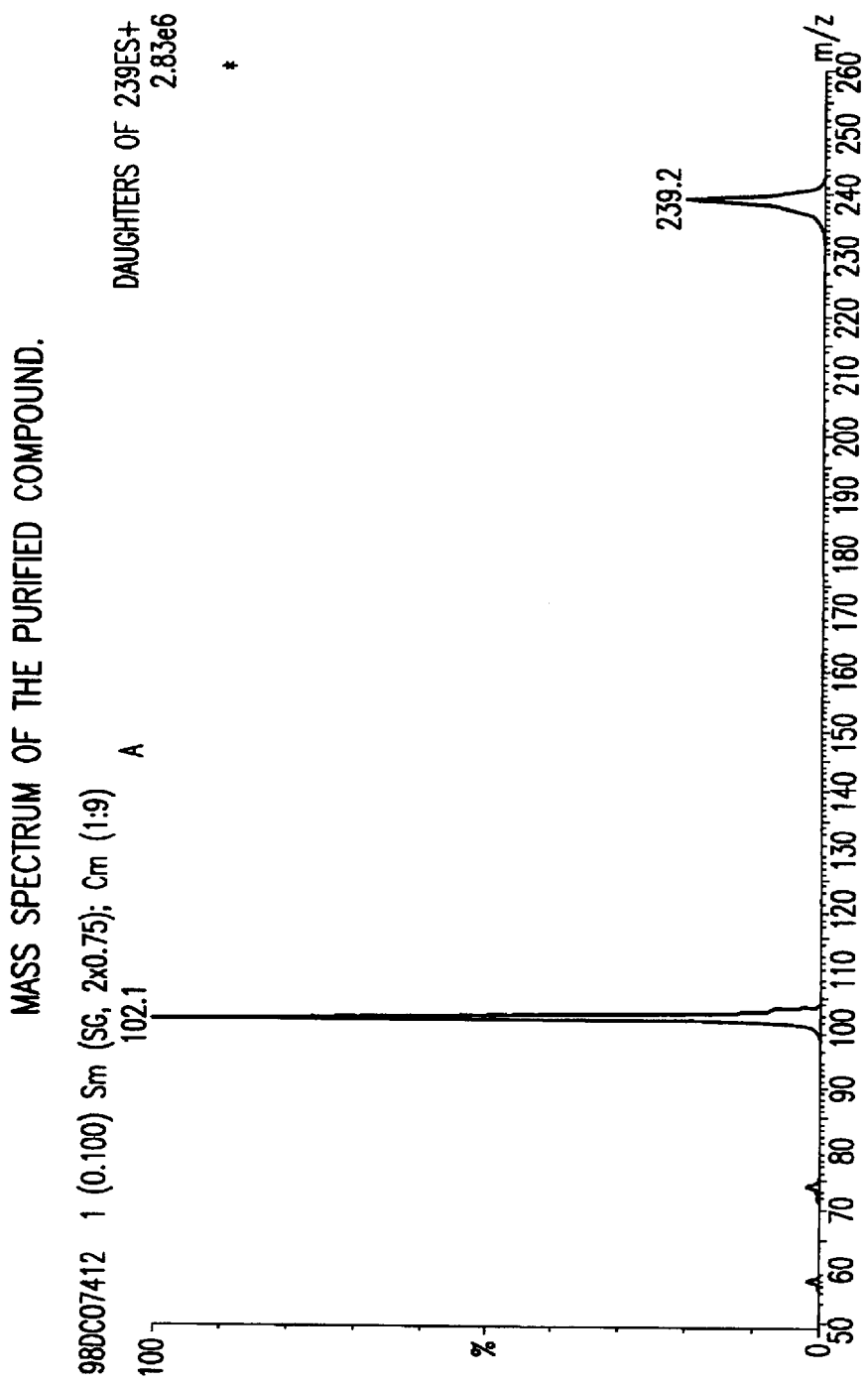
FIG. 9: Mass spectrum of the compound

+ve FABMS m/z: 239 [M]$^+$ ($C_{14}H_{25}O_2N$) (16.3), 212 (13.2), 174 (16.2), 122 (34.2), 102 (96.4), 58 (100), and 57 (19.2) (FIG. 9).

Figure 11:
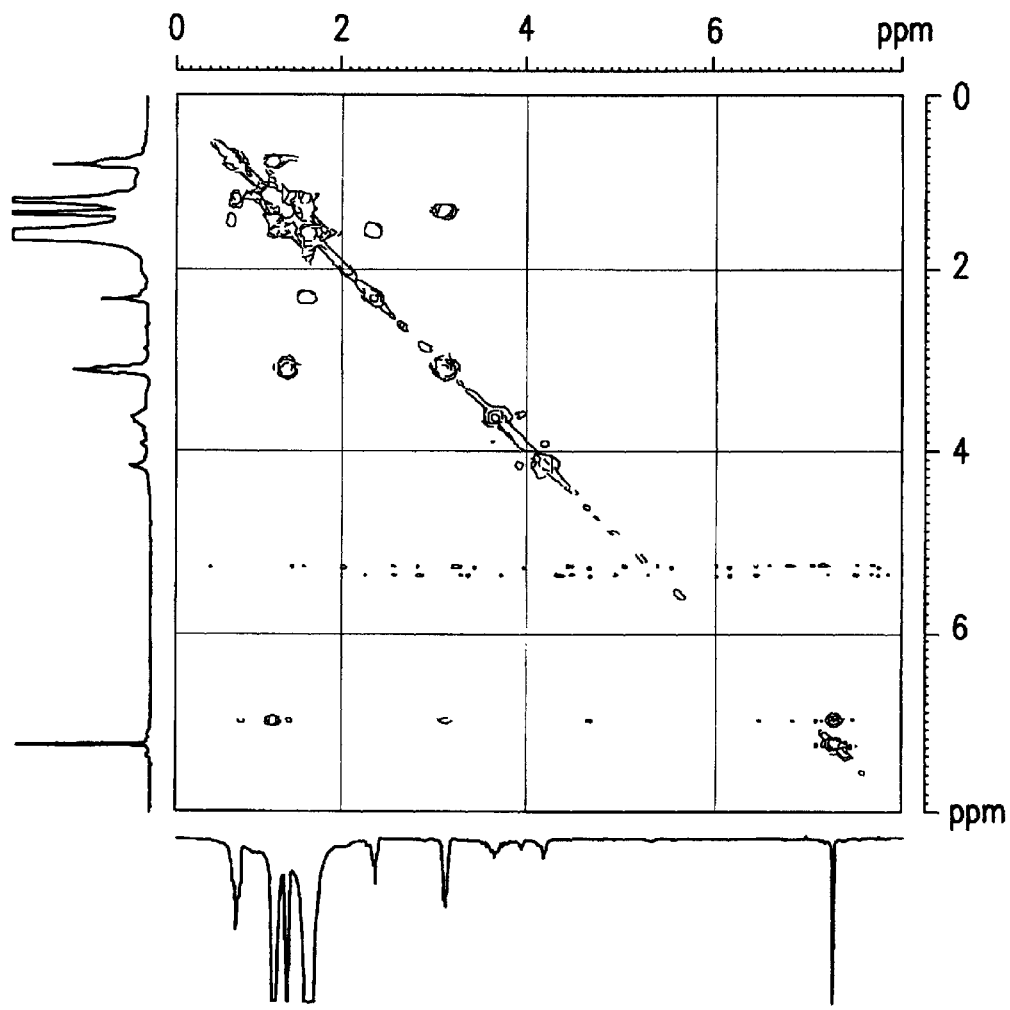
FIG. 11: COSY spectrum of the compound.

$^1$H NMR (CDCl$_3$): δ4.15 (1H, m, $C_1$—H), 3.75 (1H, m, $C_2$—H) 3.17 (2H, dd, J=7.44 Hz, 7.44 Hz, $C_5$—$H_a$ and $C_5$—$H_a$ and $C_5$—$H_b$) 2.31 (1H, t, J=6.48 Hz, $C_{2''}$—$H_a$), 1.95 (1H, m, $C_{2''}$—$H_b$) 1.62 (6H, br, $C_6$—$CH_3$ and $C_7$—$CH_3$), 1.42 (1H, d, J=6.96 Hz, $C_{2'}$—$H_a$), 1.35 (1H, d, J=7.28 Hz, $C_{2'}$—$H_b$), 1.25 (7H, br, $C_{1'}$—$CH_3$, $C_{3''}$—$H_a$, $C_{3''}$—$H_b$, $C_{4''}$—$H_a$ and $C_{4''}$—$H_b$), 0.87 (3H, t, J=5.96 Hz, $C_{5''}$—$CH_3$) and COSY spectrum (FIG. 11).

The minimum inhibitory concentration (MIC) of the said novel antifungal lead molecule is 5.0 μg/disc by disc diffusion assay (FIG. 5) and 87.5 μg/ml by percent spore germination inhibition (FIG. 6) respectively.

Figure 12:
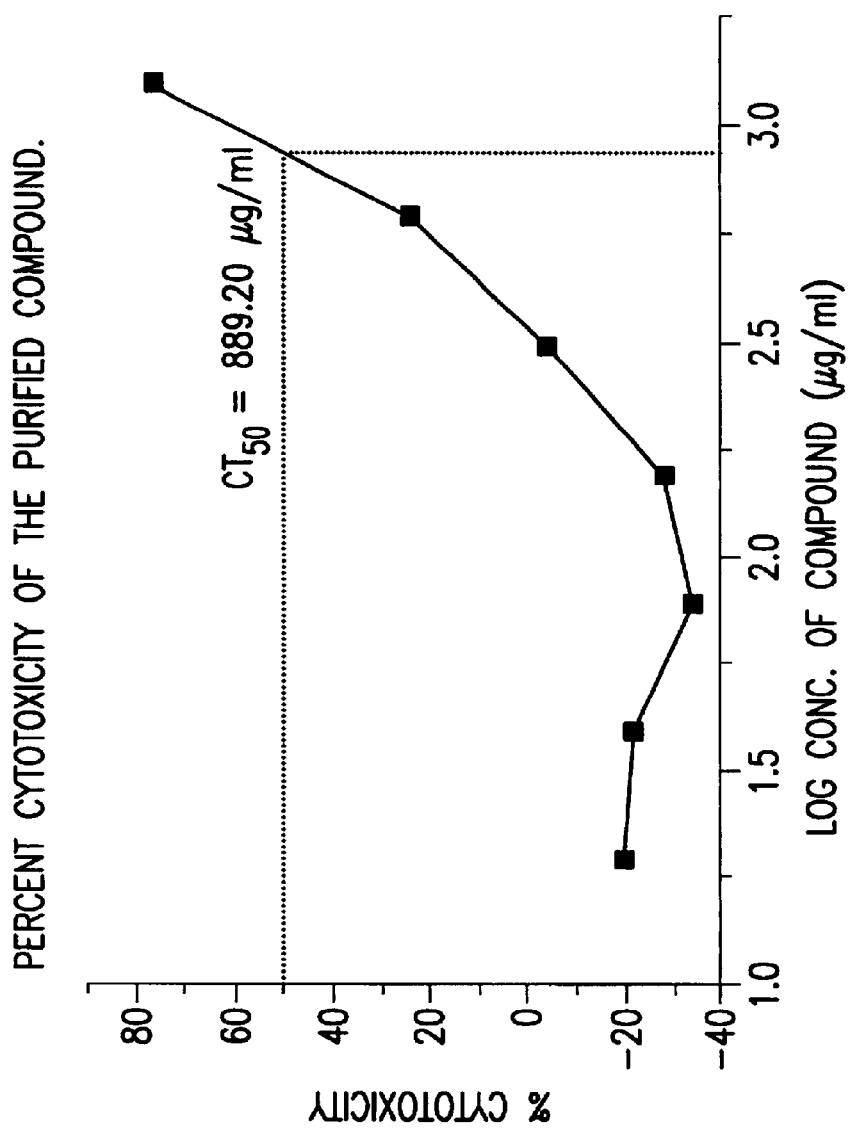
FIG. 12: Percent cytotoxicity of the compound

The dose cytotoxic to 50% of the cells ($CT_{50}$ value) of the said antifungal molecule is 889.2 μg/ml (FIG. 12).

Figure 13:
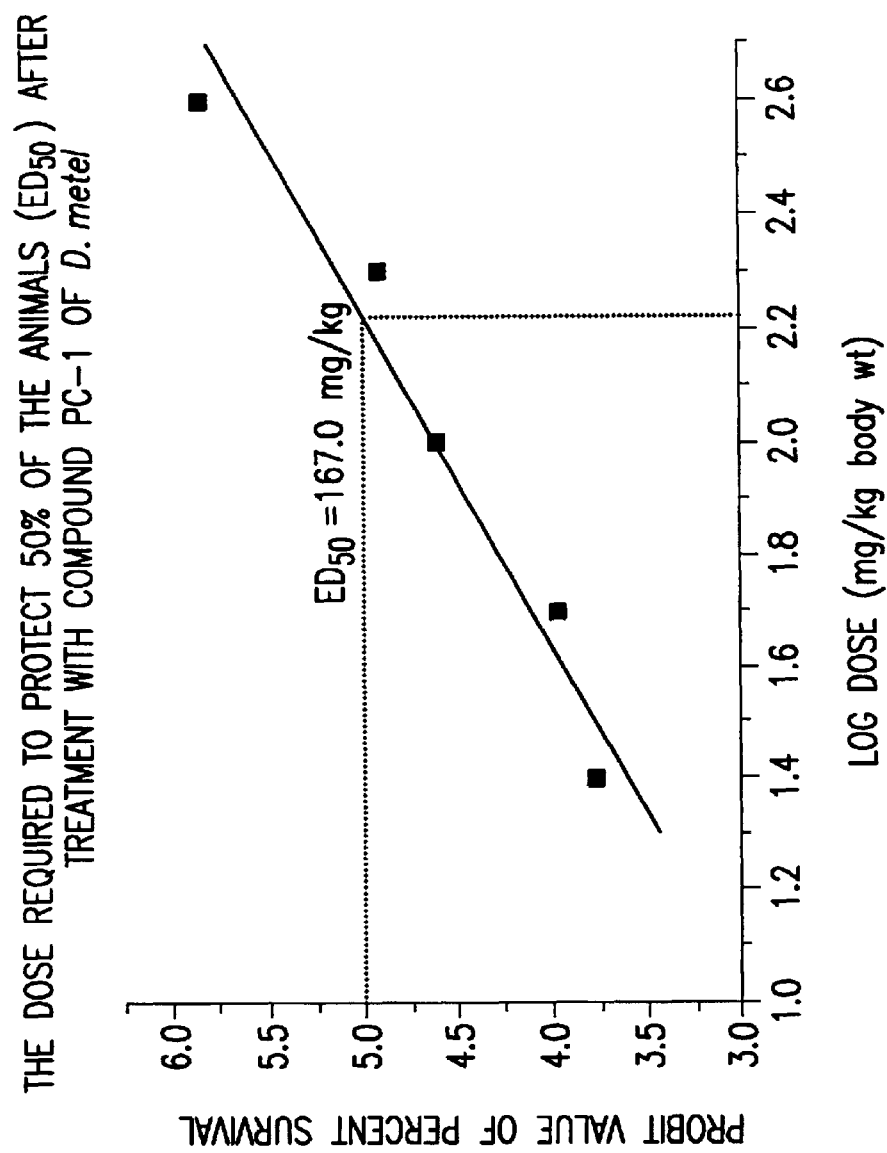
FIG. 13: The dose required to protect 50% of the animals ($ED_{50}$) after treatment with PC-1.

The $ED_{50}$ for the said antifungal compound is 167.0-mg/kg body weight (FIG. 13).

The antifungal effective dose to the said subject ranges from 100 to 400 mg/kg body weight (Table 3).

In another embodiment, the novel anti-fungal compound is 57.8 times less cytotoxic than the standard anti-fungal drug.

In further embodiment is provided a method for treatment as wherein, the dose of 2-(3,4-dimethyl-2,5-dihydro-1H-pyrrol-2-yl)-1-methylethyl pentanoate, effective for survival of 50% ($ED_{50}$) of the said subjects is 167.0 mg/kg body weight (FIG. 13).

In still another embodiment, the protective in vivo effective dose of the antifungal compound 2-(3,4-dimethyl-2,5-dihydro-1H-pyrrol-2-yl)-1'-methylethyl pentanoate to the said subject ranges from 100 to 400 mg/kg body weight (Table 3).

Yet another embodiment of the invention provides a pharmaceutical composition comprising an acceptable amount of above compound 2-(3,4-dimethyl-2,5-dihydro-1H-pyrrol-2-yl)-1'-methylethyl pentanoate with pharmaceutically acceptable additives and adjuvants.

Yet another embodiment, the acceptable additives are selected from the group of nutrients, which are pharmaceutically acceptable carrier.

Yet another embodiment, the novel antifungal molecule may be used in the form of tablet, capsule, syrup, powder, gel, ointment and injection.

Yet, another embodiment is to provide the pharmaceutically acceptable composition contains the effective amount of novel molecule at a concentration in the range of 100 to 400 mg/ml.

In still yet another embodiment, is to provide a method for the treatment of fungal infections in a said subject comprising the steps of administration of an effective amount of 2-(3,4 dimethyl-2,5-dihydro-1h-pyrrole-2-yl)-1'-methylethyl pentanoate through routes such as oral, nasal, intra venous, intra-peritoneal, intra muscular etc.

In an embodiment, the effective dose of 2-(3,4-dimethyl-2,5-dihydro-1H-pyrrol-2-yl)-1'-methylethyl pentanoate may be in the range of 100–400 mg/kg of body weight.

One more embodiment of the invention relates to a process for isolation of a novel antifungal compound 2-(3,4 dimethyl-2,5-dihydro-1H-pyrrole-2-yl)-1'-methylethyl pentanoate, from a plant, *Datura metel,* which comprises (i) extracting successively the powdered *Datura metel* plant material with an organic solvent at a temperature range of 15–45° C., (ii) removing the solvent to obtain residue, (iii) extracting the residue of step (ii) with an aliphatic hydrocarbon solvent followed by extraction with chloroform, (iv) removing chloroform from chloroform fraction of step (iii), (v) screening the residue of step (iv) obtained from chloroform fraction for antimycotic activity, (vi) isolating and purifying the novel antifungal lead molecule from active antimicotic chloroform fraction by adopting conventional chromatographic methods, and (vii) assaying the said pure lead molecule for antifungal activity and its cytotoxicity.

One more embodiment of the present invention, wherein the solvent used for extraction is selected from the group consisting of alcoholic solvent, ketonic solvent and/or halogenated hydrocarbon.

Still another embodiment of the invention, the solvent used for extraction is preferably selected from group consisting of methanol, ethanol, acetone and chloroform.

Still another embodiment of the invention, wherein the aliphatic hydrocarbon solvent used is selected from hexane, petroleum ether.

In yet another embodiment, wherein the compound is purified by using column or thin layer chromatography (TLC) and high performance liquid chromatography (HPLC).

In yet another embodiment to the invention, the purification of novel compound may be carried out by Thin Layer Chromatography using solvent systems selected from Chloroform: Acetone: Diethylamine (5.0:4.0:1.0), Chloroform: Methanol: Diethylamine (8.5:1.5:0.1) and Chloroform: Methanol: Formic acid (8.0:2.0:0.1) or different combinations of above said organic solvents.

In yet another embodiment of the invention, the purification of novel compound may be effected by HPLC using solvent system 70:30 of acetonitrile and water using reverse phase RP-8 column.

In still yet another embodiment of the invention, the characterization of active antifungal lead molecule is carried out by known analytical methods such as, using TLC, group staining reagent, infra red, ultra violet, mass and nuclear magnetic resonance spectroscopy and biological assays such as antimycotic and cytotoxic assay.

In still another embodiment, the invention provides a method of testing of novel compound (2-(3,4-dimethyl-2,5-dihydro-1H-pyrrol-2-yl)-1'-methylethyl pentanoate) as an antifungal agent.

In still yet another embodiment to the present invention, the antimycotic activity may be tested after each purification step by known methods such as microbroth dilution (MD), disc diffusion (DD) and spore germination inhibition (SGI).

Purification of the Compound

The invention provides a novel antifungal molecule 2-(3,4-dimethyl-2,5-dihydro-1H-pyrrol-2-yl)-1'-methylethyl pentanoate a process for its isolation. It particularly relates to the isolation of a novel antifungal lead molecule from natural source.

(i) Preparation of Methanolic Extract

Plant material *Datura metel* (Solanaceae) was collected during the month of April/May from near about the railway station Kishanganj, Delhi, India. Hamdard College of Pharmacy, New Delhi, authenticated the identification of plant material where voucher sample has been preserved. The freshly collected plant material was dried in the shade in a well-ventilated enclosure. Dried material was powdered and extracted with methanol. All the extracts obtained after four cycles of extraction with methanol were pooled and evaporated to dryness under reduced pressure at 45° C. in Rotavapor R-114 (Buchi) attached to a Waterbath B-480 (Buchi). The residue obtained was stored at 4° C. till use. Methanolic extract was examined for its antifungal activity against species of Aspergillus. The extract having antifungal activity was subjected to further fractionation for isolation of the active antifungal component.

(ii) Fractionation of Methanolic Extract of *Datura metel*

The constituents of crude methanolic preparation were fractionated by the method of Harbourne, with slight modifications (Harbourne J. B., 1997, Phytochemical Methods, Chapman and Hall, London, pp. 1–5). The Methanolic extract was successively extracted with hexane, chloroform and acetone respectively. The methanolic extract was first extracted with hexane four times. All the four extracts of hexane were pooled and solvent was evaporated with the help of Rotavapour R-114 (Buchi). The dry fraction was collected and kept at 4° C. till further use. The residue after the extraction with hexane was extracted stepwise with chloroform and acetone four times in each case to obtain chloroform and acetone fractions. The leftover residue was finally dissolved in methanol. Solvents were evaporated and dry fractions were recovered. All the fractions were labeled properly and examined for their antifungal activity using pathogenic species of Aspergillus. The chloroform fraction was found to be active, therefore, it was further sub-fractionated by column and thin layer chromatography.

(iii) Column Chromatography

The chloroform fraction was sub-fractionated by modified column chromatography using a silica gel column. Silica gel was suspended in hexane and packed in a glass column of 1.25×35 cm size. Slurry of chloroform extract was prepared and loaded on to the top of the pre-equilibrated silica gel (60–120µ) column. The components of chloroform fraction were eluted with 100 ml of chloroform at a flow rate of 1.0 ml/min followed by different ratio of chloroform: methanol ranging from 100:0 to 0:100. All the sub-fractions were analyzed by TLC. The sub-fractions showing similar profile of Rf values were pooled and dried in vacuo. The antifungal activity of each sub-fraction was tested using pathogenic strains of Aspergilli. The sub-fractions, which showed antifungal potential, were further subjected to the thin layer chromatography for identifying and separating out pure active component.

(iv) Thin Layer Chromatography (TLC)

The active antifungal column fractions were spotted onto the Silica gel plates (E. Merck Cat No. 1.05554, $F_{254}$) and subjected to TLC with three different solvent systems i.e. Chloroform: Acetone: Diethylamine (5.0:4.0:1.0), Chloroform: Methanol: Diethylamine (8.5:1.5:0.1) and Chloroform: Methanol: Formic acid (8.0:2.0:0.1). The bands on the plates were visualized with UV light at 254 nm and 366 nm and by spraying with Chloropalatinate, Dragendorff reagent and Iodine. The components in different bands were scrapped and examined for antifungal activity. The preparative TLC was performed to obtain active component of our interest.

(v) High Pressure Liquid Chromatography (HPLC)

The purity of the compound PC-1 obtained from preparative TLC was analyzed by HPLC using RP-8 column (Merck). The reverse phase HPLC was performed isocratically with the solvent system 70 parts acetonitrile: 30 parts water. The test samples were passed through a membrane of pore size before loading. 5.0 µl of the 0.22µ filtered sample was loaded on to the pre-equilibrated HPLC column at room temperature. The flow rate was maintained at 1.0 ml/min.

Characterization Studies (i) Structure Elucidation

Figure 10:
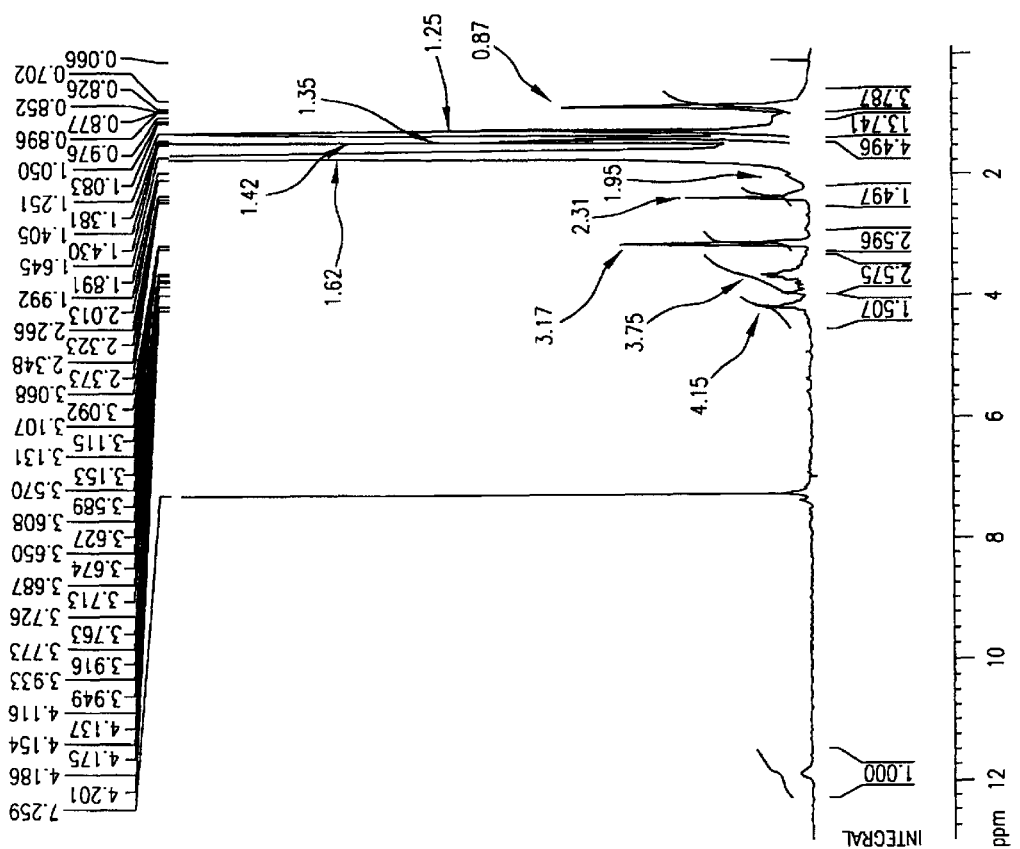
FIG. 10: NMR spectrum of the compound.

Characterization of the compound was carried out using various techniques such as class identification by chemical methods, derivatisation of the compound, melting point of the purified compound, ultraviolet spectrum (FIG. 7), infra red spectrum (FIG. 8), mass spectroscopy (FIG. 9), nuclear magnetic resonance spectrum (FIG. 10) and, COSY (FIG.

11). Details of the spectral data obtained with respect to novel compound are as described earlier.

Antifungal Activity Assays

The antifungal activity of various fractions such as crude, methanolic extract, sub-fractions and purified compound was studied by microbroth dilution, disc diffusion and spore germination inhibition assays using pathogenic strains of fungi.

(i) Pathogen

Pathogenic strains of fungi were obtained from the Mycology Department of Vallabhbhai Patel Chest Institute, Delhi. All the strains were grown on Sabouraud dextrose agar at 37° C. The conidia form these cultures were harvested and suspended in Sabouraud maltose broth. The number of conidia was counted using haemocytometer and their number in the suspension was adjusted to as per need of the experiment.

(ii) Microbroth Dilution Assay

The antifungal susceptibility of the fungi to various fractions or the purified component was assayed by the microbroth dilution method (Forthergill A. W. and McGough A. W., 1995, Clin. Microbiol. Procedure Handbook. In Vitro susceptibility Testing of Yeast, 5.15.1–5.15.15). The fungal spores were harvested from 96-h cultures and their number adjusted to $1 \times 10^6$ per ml. The Sabouraud Dextrose medium was dissolved in glass double distilled water and autoclaved at 10 psi for 15 min. 90-$\mu$l medium was added into the wells of cell culture plates. The different concentrations of the extract, fractions or the purified compound were prepared in duplicate wells and then the wells were inoculated with 10 $\mu$l of spore suspension. The plates were incubated at 37° C. and examined macroscopically after 48 h for the growth of fungal mycelia. The activity was represented as –ve if growth was there and +ve if medium appeared clear with out any growth of fungi.

(iii) Disc Diffusion Assay

The disc diffusion test was performed in 10 cm diameter (Tarsons) radiation sterilized petri plates as per the method described in Indian Pharmacopoeia (Indian Pharmacopoeia, 1996, Appendix 9, p A101–A110). Sabouraud Dextrose agar medium was dissolved in double glass-distilled water and autoclaved at 10 psi for 15 minutes. It was cooled to 45° C. and 20.0 ml was poured into each petri dish. $1 \times 10^6$ conidia in 1.0 ml of conidial suspension were prepared in Sabouraud maltose broth and overlaid on the surface of the agar plate.

Different concentrations of the samples were impregnated on the sterilized discs measuring 5.0 mm in diameter from Whatman filter paper number. The discs were placed on the surface of the agar plates already inoculated with the fungal spores. The plates were incubated at 37° C. and examined at 48 hrs for zone of inhibition, if any, around the disc. The diameter of zone of inhibition was measured with the help of a scale. The concentration, which developed the zone of inhibition of 6.0-mm diameter, was considered as minimum inhibitory concentration. Amphotericin B was used in assay as a standard control drug. An additional control disc without any sample but impregnated with equivalent amount of solvent was also used. The test was repeated three to five times with various test preparations of plant to ascertain activity.

(iv) Preparation of Standard Curve

Standard curve was prepared in accordance with the method given in the Indian Pharmacopoeia (Indian Pharmacopoeia, 1996, Appendix 9, p A101–A110).

(v) Spore Germination Inhibition Assay

The modified spore germination inhibition assay was performed as described earlier (Sureder P. and Janaiah C., 1987, Ind. J. Expt. Biol., 25, 233–234). The fungal species were grown on Sabouraud dextrose agar plates at 37° C. for 96 h. Conidia were harvested from the plates and their homogenous suspension was prepared in the Sabouraud dextrose broth. The conidia were counted and their number in the suspension was adjusted to $1 \times 10^4$ per ml. The standard drug Amphotericin B and test samples were initially dissolved in minimal quantity of dimethylsulfoxide (DMSO) and then diluted with Sabouraud dextrose medium. Various concentrations of the test samples in 90 $\mu$l of culture medium were prepared in 96 well flat bottom micro-culture plates (Nunc) by double dilution method. The wells were prepared in triplicates for each concentration. Each well was then inoculated with 10 $\mu$l of spore suspension containing 100±5 spores. The plates were incubated at 37° C. for 10 h and then examined for spore germination under inverted microscope (Nickon Diphot). The number of germinated and non-germinated spores was counted. The percent spore germination inhibition (PSGI) was calculated using following formula $$PSGI = 100 - \frac{\text{No. of spores germinated in drug treated well}}{\text{No. of spores germinated in control well}} \times 100$$

In vitro Toxicity Evaluation

The in vitro toxicity of the active molecule was studied by MTT assay using RAW cells (Mossman, T., 1983, J. Immunol. Methods, 65, 55–63).

Cell Culture:

The stock culture of RAW cells was obtained from National Facility for Cell and Tissue Culture, Pune. Cells were maintained in RPMI-1640 medium supplemented with glutamine (2.3 gm/L), fetal calf serum (10% v/v) and gentamycin (50.0 mg/L) at 37° C. in Nuair IR Autoflow water Jacketed carbon dioxide incubator.

Sample Preparation:

The stock solution of the compound was prepared by dissolving 2.5 mg of the purified compound in minimum amount of DMSO and then diluted with double distilled water to make the final volume 1.0-ml. The different concentrations ranging from 1250.0 $\mu$g/ml to 19.5 $\mu$g/ml were tested in the cytotoxicity assay.

Cell Cytotoxicity Assay:

The cells were harvested at the log phase of growth confluency from the flask. The homogeneous suspension of cells was prepared in 2.0 ml of culture medium. The number of cells in the suspension was counted using a hemocytometer and the cell suspension was diluted in such a way so as to obtain $5 \times 10^7$ viable cells per ml. The viability of the cells was checked with trypan blue dye exclusion test. The cytotoxicity assay was performed in 96 wells flat bottom tissue culture plates (Nunc Nunclon). The cells ($5 \times 10^6$) in 100.0 $\mu$l volume were seeded into each well. The plate was incubated at 37° C. in atmosphere of 5% (v/v) $CO_2$ for 8 h. The wells were examined microscopically for the formation of monolayer of the cells. Various concentrations ranging from 1250.0 $\mu$g/ml to 19.5 $\mu$g/ml of the compound PC-1 (metelatropinyl ester) were added to the monolayer of cells. In +ve control wells, a known cytotoxic protein obtained from A. fumigatus, was used. The $ZnSO_4$ (8.0 mg/L) was used as another +ve toxic material in another set of wells. In negative control wells equivalent amount of the solvent was used. The duplicate wells were used for each concentration of the test compound. The plates were incubated at 37° C. in 5% (v/v) $CO_2$ incubator overnight (12 h). The medium along with floating dead cells from the wells was removed by inverting the plate. Thus, only the live cells sticking to the surface of plate were left in the wells. The cells were stained with 40.0 μl of 2.5% dye MTT. After adding the dye to the wells, the plate was kept at 37° C. in 5% $CO_2$ for 1 h. The tissue culture plate was removed from the incubator and all the dye was aspirated. Only live cells took up the dye. The cells were lysed by adding 100.0 μl of isopropanol-HCl to the wells. After lysis of the cells, the plates were read at 540 nm using plate reader (Spectra Max 190, Molecular Device).

Interpretation of Results:

The toxicity of the compound was expressed as percentage with respect to that obtained in –ve control sample. The percent cytotoxicity was calculated using the formula given below.

$$\% \text{ Cytotoxicity} = \frac{\text{OD in -ve control} - \text{OD in the test}}{\text{OD in -ve control}} \times 100$$

In vivo Efficacy of PC-1

In vivo efficacy of the compound against *A. fumigatus* infection was studied in the Balb/C mice of 6–8 weak of age of either sex, weighing 15–20 g each. The mice model of aspergillosis described by Dixon et al (1989), was used to study the effects of compound on in vivo infection of *A. fumigatus*.

The animals were housed in the micro-barrier cages on sterile bedding and fed ad libitum water and food. The mice were divided into 6 groups and each group contained 8–10 animals. The mice were infected experimentally with *A. fumigatus*. Three days prior to infection with conidia, mice were injected subcutaneously with 3 doses (250.0 mg/kg/day) of cortisone acetate in 400.0 μl of PBS. On the infection day, each mouse received $2 \times 10^7$ conidia by nasal instillation of a single droplet of conidial suspension. The animals of this model developed invasive aspergillosis and all the infected animals died within 4–6 days.

Inoculum Prepration for *A. fumigatus* for Experimental Infection to Mice:

*A. fumigatus* (190/96) isolate was grown on Sabouraud dextrose agar plates at 37° C. for 4 days. The conidia were collected from the culture plates using PBS (pH 7.2) containing 0.05% Tween 80 (Sigma Chemicals) and the suspension was filtered through sterile glass wool. The conidia were pelleted by centrifugation at 2000 rpm and re-suspended in PBS, pH 7.2. The number of conidia was counted and adjusted to $1 \times 10^8$ conidia/ml. The viability of the conidia was determined by plating the dilutions of suspensions on Sabouraud dextrose agar.

The purified compound (metelatropinyl ester) isolated from the *D. metel* was administered orally in the concentration ranging from 0.0, 25.0 50.0 100.0 200.0 and 400.0 mg/kg body weight to the mice infected experimentally with *A. fumigatus*.

Treatment:

The dosing of the animals (cortisone treated and challenged) with compound in 6 different groups was initiated within 30 min after challenge with *A. fumigatus* conidia.

Group I: The mice were treated orally with 7 doses of 25.0 mg/kg/day of the compound.

Group II: The animals infected with *A. fumigatus* conidia were given 50.0 mg/kg/day of the compound for 7 days orally.

Group III: The animals in this group were given 7 oral doses of 100.0 mg/kg/day of the compound.

Group IV: In this group of animals, 7 oral doses of the compound (200.0 mg/kg/day) were given.

Group V: The animals of this group were treated with 7 doses of 400.0 mg/kg/day orally over a period of 7 days.

Group VI: The animals of this group acted as control and were treated orally with 7 doses of 400 μl PBS containing solvent.

Survival Rate:

The animals were housed in properly labeled cages and kept under close watch for weight loss and the mortality. The survival rate over a period of 10 days was calculated and the fungal burden in survivors determined (Clemons and Stevens, 1994). Of the animals treated with doses of 25.0, 50.0, 100.0, 200.0 and 400.0 mg/kg body weight, 1 out of 10 (10%), 1 out of 8 (12.5%), 3 out of 9 (33.3%), 4 out of 9 (44.4%) and 8 out of 10 (80%) respectively, survived up to $10^{th}$ day.

Quantification of Colony Forming Units:

The mice were kept under constant watch and those getting moribund, dying or survived up to 10 days were sacrificed. The autopsy was performed on the mice who had died to remove their organs for quantification of colony forming units (CFU). The lungs, livers and kidneys of the mice were removed aseptically, placed in sterile PBS (pH 7.2) and homogenized with teflon pestle mortar. The CFU in the animals were determined by plating 10 fold dilutions of organ homogenates on Sabouraud dextrose agar containing 0.05% triton X-100. The triton X-100 limited the colony size and thus greatly facilitated colony counting (Frosco, 1992). After an incubation for 48 h at 37° C., colonies were counted and results were expressed as CFU per organ.

The survival time and CFU indicating the fungal burden in various organs were considered to evaluate the protective efficacy of the compound in vivo.

The following examples are given by way of illustration of the present invention and should not be construed to limit of the scope of the present invention.

EXAMPLE 1

Extraction and Fractionation

Aerial parts of the plant *Datura metel* (Solanaceae) were collected during the month of April from an area around Delhi, India. Hamdard College of Pharmacy, New Delhi, authenticated the identification of plant material where voucher sample has been preserved. The freshly collected plant material was dried in the shade in a well-ventilated enclosure. 400 gm dried material was powdered and extracted with 500 ml methanol in each cycle. All the extracts obtained after four cycles of extraction were pooled and evaporated to dryness under reduced pressure. The 25 gm residue was obtained and stored at 4° C. till use.

The methanolic extract was successively extracted with hexane, chloroform and acetone. The methanolic extract was first extracted with hexane four times. All the four extracts of hexane were pooled and solvent was evaporated. The dry hexane fraction was collected and kept at 4° C. till further use. The residue after the extraction with hexane was extracted stepwise with chloroform and acetone four times in each case to obtain chloroform and acetone fractions respectively. The leftover residue was finally dissolved in methanol. Dried fractions were examined for their antifungal activity. The fractions, which did not inhibit the growth of Aspergillus up to a concentration of 1500 μg/ml and 50 μg/disc in spore germination inhibition and disc diffusion assays respectively, were considered to be non-active. The chloroform fraction of *Datura metel* was found to be active as a concentration of 1250 μg/ml inhibited the germination of 100% of the spores in spore germination inhibition assay and a concentration of 25.0 μg/disc produced the zone of inhibition of activity significance. Therefore, this fraction was further used to identify and purify the active component using various chromatographic methods.

EXAMPLE 2

Purification of Active Compound

The chloroform fraction was sub-fractionated by modified column chromatography as described above. The above said fractions were analyzed by TLC and those showing similar spots were pooled and dried in vacuo to get sub-fractions. Total 15 sub-fractions were obtained. The antifungal activity of each sub-fraction thus obtained was tested using pathogenic strains of Aspergillus. The sub-fraction numbers 10 and 11 showed potential antifungal activity and they were further subjected to preparative thin layer chromatography for separating the pure active component.

Silica gel plates (Cat No. 1.05554, $F_{254}$) were purchased from E. Merck and used for performing TLC. The column chromatographic active sub-fractions were spotted onto the plates and subjected to run with three different solvent systems i.e. chloroform: acetone: diethylamine (5.0:4.0:1.0), chloroform: methanol: diethylamine (8.5:1.5:0.1) and chloroform: methanol: formic acid (8.0:2.0:0.1). The bands on the plates were visualized with UV light at 254 nm and 366 nm and by spraying with chloropalatinate, Dragendorff reagent and iodine. The components in three different major bands resolved with a solvent system chloroform: methanol: formic acid (8.0:2.0:0.1) (FIG. 1) having Rf values 0.14, 0.22 and 0.37 respectively were scrapped and examined for antifungal activity. The compound, which had efficacy against Aspergillus, was recovered from a band having Rf value of 0.22. The compound was purified by repeated preparative TLC and tested for its antifungal activity. The active compound reacted positively with Dragendorff's reagent showing thereby its alkaloidal nature.

Figure 2:
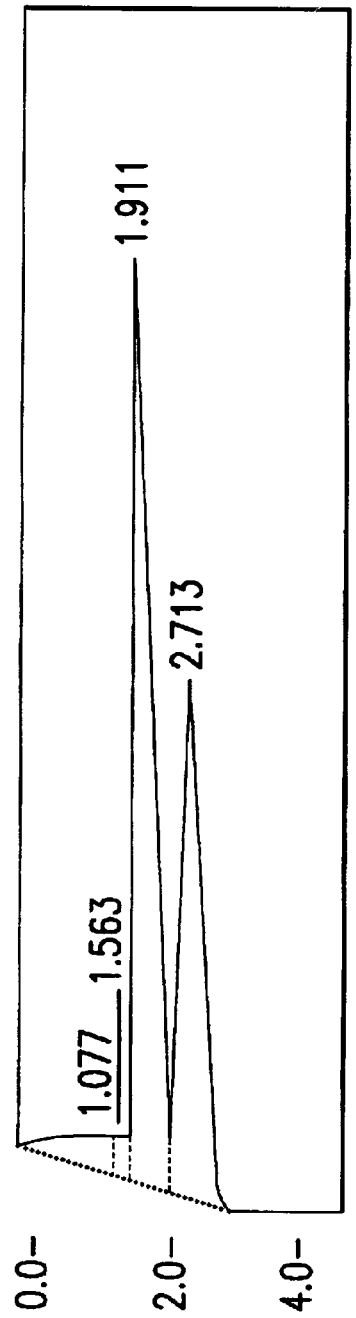
FIG. 2: HPLC profile of TLC purified compound
Figure 3:
FIG. 3: Photograph of TLC of HPLC purified compound.
Figure 4:
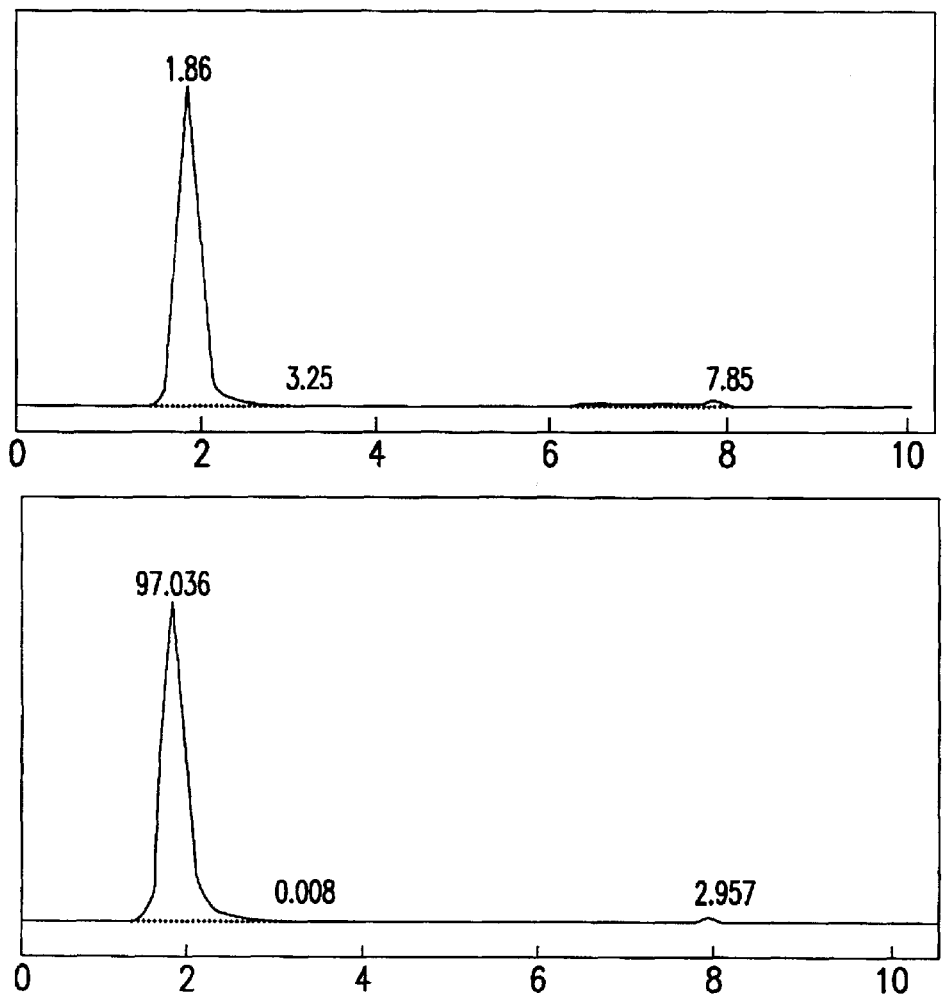
FIG. 4: HPLC profile of purified compound.

The purity of the compound obtained from preparative TLC was analyzed by HPLC using RP-8 column (Merck). The reverse phase HPLC was performed isocratically with the solvent system acetonitrile: water (70:30). Samples were passed through a membrane of 0.22μ pore size before loading. A total of 5.0 μl of the sample was loaded on to the pre-equilibrated column at an ambient temperature. The flow rate was maintained at 1.0 ml/min. The HPLC profile of compound purified by TLC showed two peaks, peak-I and II, which had retention times 1.91 mts. and 2.71 mts. respectively (FIG. 2). These two corresponding peaks at retention time 1.88 mts. and 2.84 mts respectively were present in the HPLC profile of active sub-fraction obtained from the column chromatography also. The active column sub-fraction had five major peaks corresponding to retention time 1.31, 1.88, 2.84, 3.82 and 4.35 mts respectively. Changing the solvent system in TLC carried out the further purification of partially purified compound. The solvent system comprised of chloroform: methanol: diethylamine (8.5:1.5:0.1) resolved the mixture containing active molecule having $R_f$ at 0.42 (FIG. 3). The retention time of compound in HPLC was found to be around 1.9 mts. and it was showing purity from 97% to 100% in various runs (FIG. 4). The retention time of the compound remained same in both chromatographic active sub-fraction and its purified form.

EXAMPLE 3

Antifungal Activity of Pure Compound by Microbroth Dilution Assay

The antifungal susceptibility of the fungi to the purified compound was assayed by the microbroth dilution method. The different concentrations of the purified compound ranging from 21.87 to 350 μg/ml were prepared in duplicate wells by twofold dilution method. The test was done as described above. The antifungal activity of the compound is given in the Table 1. The MIC of the compound was found to be 87.5 μg/ml. At this concentration of compound none the three species of Aspergillus showed any visual growth in wells.

TABLE 1

Activity of the compound against Aspergillus sp. after 48 hrs.

| Concentration of compound (μg/ml) | A. fumigatus | A. niger | A. flavus |
| --- | --- | --- | --- |
| 350.00 | + | + | + |
| 175.0 | + | + | + |
| 87.50 | + | + | + |
| 43.75 | − | − | − |
| 21.87 | − | − | − |

EXAMPLE 4

Antifungal Activity of Pure Compound by Disc Diffusion Assay

Figure 5:
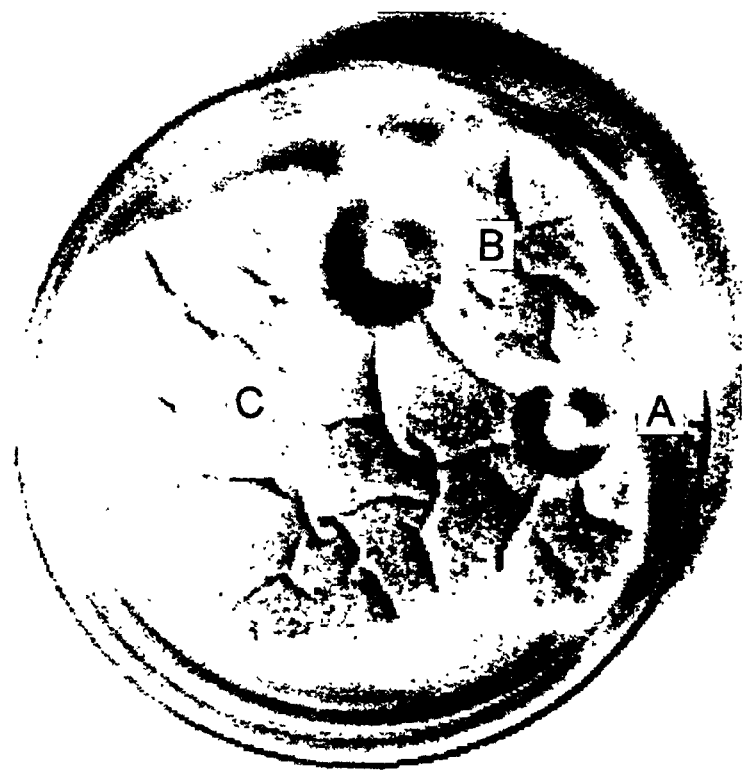
FIG. 5: Inhibition of growth of *A. fumigatus* by purified compound.

The disc diffusion test was performed as per described in the section of details of invention. Amphotericin B 1.25 μg/disc was used in assay as positive control standard drug. Additional discs impregnated with equivalent amount of solvent were also used in the assay as negative controls (FIG. 5). The MIC of the compound was observed to be 5 μg/disc, since this concentration developed zone of inhibition having mean diameter of 6.25, 6.15 and 6.4 mm against A. fumigatus, A. flavus and A. niger respectively (Table 2).

TABLE 2

Antifungal activity of compound by disc diffusion method

| Concentration, | Diameter of zone of inhibition (mm) | | |
| --- | --- | --- | --- |
| (μg/disc) | A. fumigatus | A. flavus | A. niger |
| 20.0 | 9.25 | 9.00 | 9.40 |
| 10.0 | 8.50 | 8.10 | 8.60 |
| 5.0 | 6.25 | 6.15 | 6.40 |
| 2.5 | — | — | — |
| Solvent control | — | — | — |

EXAMPLE 5

Comparison of Antifungal Activity of Compound with that of Amphotericin B

Figure 6:
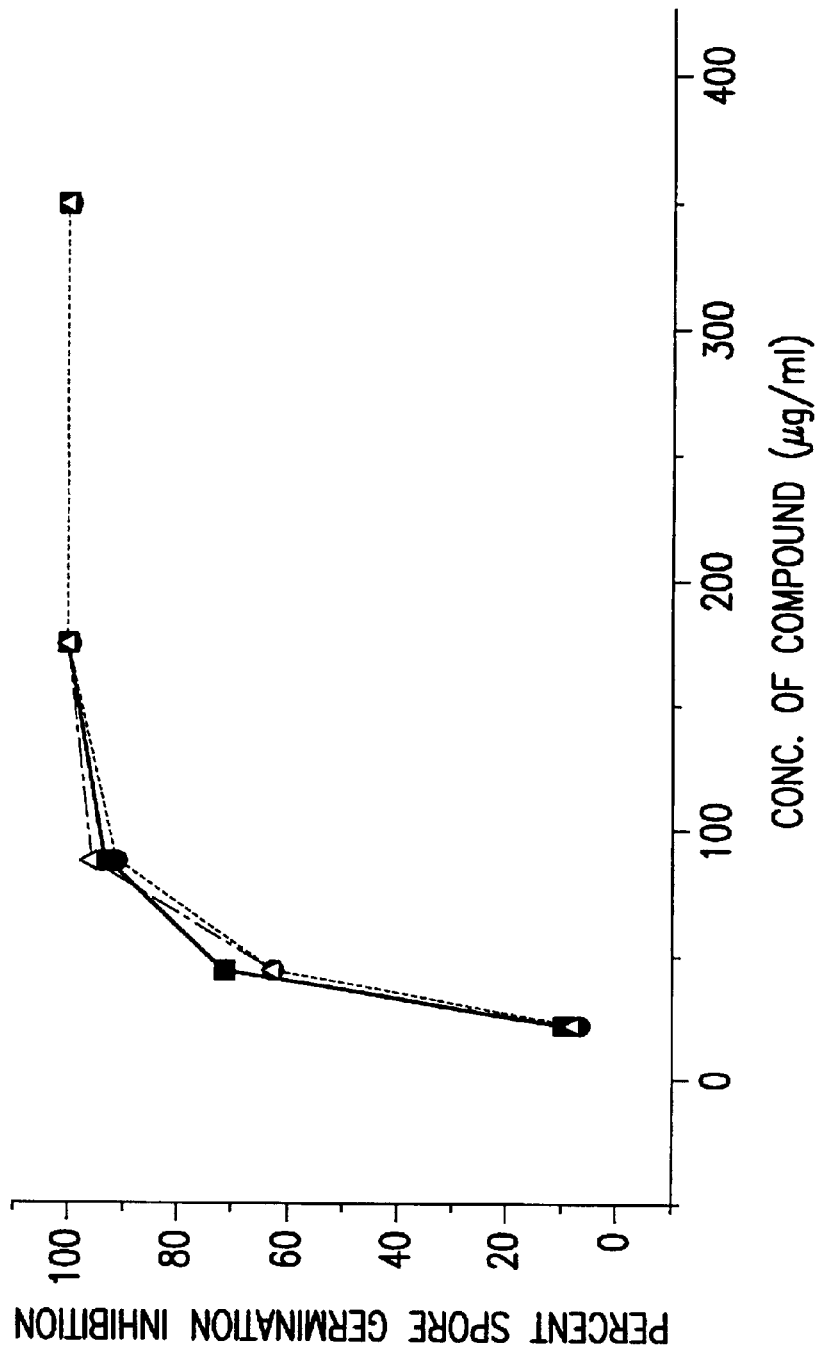
FIG. 6: Graph represents the percent spore germination inhibition by the compound against Aspergillus species.

The potency of the compound was determined with the help of standard curve constructed using amphotericin B as standard drug against A. fumigatus. Standard curve was prepared according to method given in the Indian Pharmacopoeia. The corrected values of diameter of zone of inhibition along with lowest and highest values were determined. These values were plotted on semilog paper to prepare standard curve. The value of diameter of zone of inhibition obtained for compound was put into the standard curve and corresponding dose producing the effect equivalent to amphotericin B was determined to find out the potency of the compound (FIG. 6).

A concentration of 10 μg/disc of the compound produced a diameter of zone of inhibition equivalent to that produced by 2.67 μg of amphotericin B. These observation showed that the compound was 3.74 time less potent as compared to amphotericin B, but more importantly it is a novel lead molecule.

EXAMPLE 6

Antifungal Activity of Pure Compound by Spore Germination Inhibition Assay The spore germination inhibition assay was performed to evaluate the activity of the compound. Various concentrations of the compound ranging from 21.875 to 700 µg/ml in 90 µl of the culture medium were prepared by double dilution method. Wells were inoculated with 10 µl of spore suspension and incubated at 37° C. for 10 hrs. The number of germinated and non-germinated spores was counted and the percent spore germination inhibition (PSGI) was calculated. The percent spore germination decrease with increased dose of the compound. The MIC of the compound was found to be 87.5 µg/ml (FIG. 6).

EXAMPLE 7

Cell Cytotoxicity

The in vitro cell cytotoxicity of the compound PC-1 was investigated by incubating RAW cells with varying concentrations of PC-1 and measuring the extent of cytotoxicity by MTT assay as described above. A concentration of compound up to 312.5 µg/ml was completely non-toxic to the cells. The higher doses of the compound developed variable toxicity. A concentration of 1250.0 µg/ml of the compound was toxic to 75.95% of the cells. The percent cytotoxicity was plotted against log concentration of the compound to find out concentration which was cytotoxic to 50% of the cells ($CT_{50}$). The $CT_{50}$ of the compound was found to be 889.2 µg/ml (FIG. 12).

EXAMPLE 8

Structure Elucidation of the Compound

Correlating all the spectral and chemical analysis information of the compound, the applicants have carried out the characterization of the compound.

(i) UV Spectroscopic Data

The compound PC-1, named metelatropinyl ester, showed two maxima in the UV spectrum, which had λ max 300 and 206 nm and absorbance 0.250 and 1.676 respectively. The prominent maxima at 206 nm in UV spectrum might be due to the presence of ester group. The λ max for ketone has been shown to be 208 nm or little higher. Therefore, the peak at 206 nm suggested the presence of ester group in the PC-1.

(ii) IR Spectroscopic Data

The IR spectrum exhibited absorption bands for amino group (3434 $cm^{-1}$), ester group (1711, 1230 $cm^{-1}$), and unsaturation at 1646 $cm^{-1}$ (FIG. 8).

(iii) Mass Spectroscopic Data

The molecular mass of the compound was found to be 239.2 on the basis of its FAB mass spectrum and the intensity of the peak was found to be 20%. The calculations made on the basis of peak intensity at m/z 239.2 (20) in the mass spectrum revealed the presence of 13.8 (=14) carbon atoms in the molecule PC-1 (Furniss et al, 1989; Kemp, 1991). The chemical analysis and mass spectrum of PC-1 indicated the presence of at least one nitrogen and two oxygen atoms in the compound. The chemical formula thus derived for the compound PC-1 turned out to be $C_{14}H_{25}O_2N$. The nitrogen rule also supported the presence of single nitrogen atom in the molecule. The molecular weight derived from the chemical formula was found 239.188, which indeed was the same as shown by the mass spectrum. The mass spectrum of compound displayed the base peak at m/z 58 generated due to $C_1$–$C_2$ and OC—O fission, suggesting secondary nature of the tropane ring. A prominent ion peak at m/z 102 arose due to formation of pentanoic acid moiety ($C_5H_{10}O_2^+$). Cleavage of $C_1$–$C_{2'}$ linkage resulted in the formation of an ion peak at m/z 57 ($C_4H_9^+$) (FIG. 9).

(iv) NMR Spectroscopic Data

The $^1$HNMR spectrum displayed multiplets al. δ4.15 and 3.75 assigned to —CH—O— and —N—CH protons respectively. A double doublet at δ3.17 assigned to —N_CH protons. A triplet at 3.17 assigned to —N—CH$_2$ protons. A triplet at δ2.31 and a multiplet at δ1.95 of one proton each is assigned to —C—CH$_2$ protons. A broad six proton signal at δ1.62 is attributed to –CH$_3$ group protons attached at positions 3 and 4 of dihydropyrrol ring. Two doublet of one proton each at δ1.35 and 1.42 are assigned to —CH$_2$ proton attached to 2-position of dihydropyrrol ring. A seven proton broad signal is assigned to 2x-CH$_2$ (each proton of pentanoic side chain, —CH$_3$ (three protons) of —CO—CH—CH$_3$ group and a triplet at δ0.87 for three protons is assigned to terminal —CH$_3$ group of pentanoil acid. The absence of any signal beyond δ4.15 suggested tetrasubstituted olefinic linkage in the molecule. The existence of a methyl group linked to endo-nitrogen atom was resulted out due to absence of any signal between δ2.0 and δ3.0 in the $^1$H NMR spectrum. In $^1$H—$^1$H 2D COSY spectrum the correlation between hydrogen atoms of the dihydropyrrol ring was established (FIG. 11).

Based on these evidences the structure of the molecule has been elucidated as 2-(3,4-dimethyl-2,5-dihydro-1H-pyrrol-2-yl)-1-methylethyl pentanoate.

The molecule PC-1 identified in the present investigation as 2-(3,4-dimethyl-2,5-dihydro-1H-pyrrol-2-yl)-1-methylethyl pentanoate is a new tropine derivative and the occurrence of this molecule is being reported for the first time from a plant or synthetic source. This is a novel antifungal compound useful as a lead molecule for the development of new antimycotic drugs. The $CT_{50}$ of amphotericin B and its liposomal derivatives (drug of choice) was reported to be in the range of 4.0–64.0 µg/ml (Zager, R. A., 2000, Am. J. Kidney Dis., 2, 238). The $CT_{50}$ value of novel compound is 889.2 µg/ml which indicated the compound to be many fold less cytotoxic than the amphotericin B.

EXAMPLE 9

In vivo Efficacy

The Balb/C mice of 6–8 weak of age of either sex, weighing 15–20 g, were housed in micro-barrier cages on sterile bedding and fed ad libitum water and food. The animals were divided into 6 groups and each group contained 8–10 mice. The efficacy of PC-1 against aspergillosis was studied at five dose levels. Various doses of the compound were administered orally to the animals already challenged with $2 \times 10^7$ spores of A. fumigatus shows the survival rate of the animals treated with compound. Of the animals treated with doses of 25.0, 50.0, 100.0, 200.0 and 400.0 mg/kg body weight, 1 out of 10 (10%), 1 out of 8 (12.5%), 3 out of 9 (33.3%), 4 out of 9 (44.4%) and 8 out of 10 (80%) respectively, survived up to $10^{th}$ day.

The percent survival rate in treated animals increased with the dose, indicating thereby the protective efficacy to be dose dependent. The probit values of percent survival were plotted against log dose of the compound PC-1 on the semilog paper to determine the effective dose required to confer protection in 50% of the animals ($ED_{50}$). The $ED_{50}$ of the compound PC-1 was found to be 167.0 mg/kg body weight (FIG. 13).

EXAMPLE 10

Quantification of Colony Forming Units

The mice were kept under constant watch and those getting moribund, dying or survived up to 10 days were sacrificed. The autopsy was performed on the mice who had died to remove their organs for quantification of colony forming units (CFU). The lungs, livers and kidneys of the mice were removed aseptically, placed in sterile PBS (pH 7.2) and homogenized with teflon pestle mortar. The CFU in the animals were determined by plating 10 fold dilutions of organ homogenates on Sabouraud dextrose agar containing 0.05% triton X-100. The triton X-100 limited the colony size and thus greatly facilitated colony counting (Frosco, 1992). After an incubation for 48 h at 37° C., colonies were counted and results were expressed as CFU per organ.

The survival time and CFU indicating the fungal burden in various organs were considered to evaluate the protective in vivo efficacy of the compound 2-(3,4-dimethyl-2,5-dihydro-1H-pyrrol-2-yl)-1-methylethyl pentanoate.

The fungal burden in the organs of the animals, which died or became moribund during study or those survived up to $10^{th}$ day, was determined. The lungs, livers and kidneys of the animals were isolated, homogenized and the homogenate was used to culture the pathogen on Sabouraud dextrose agar plates. The colonies of the fungus were counted and expressed as colony forming units (CFU)/organ. Table 3 shows the number of CFU in different organs.

The doses of 25.0 and 50.0 mg/kg body weight did not have any effect on the CFUs in the lung tissue. However, protective effect was observed in animals treated with higher doses. A dose of 400 mg/kg body weight of PC-1, reduced the colony counts significantly as compared to controls. The difference was found to be statistically significant (p<0.001). The liver was found to have least burden of fungus and there was very less effect of the compound on CFUs in liver. The kidneys appeared to be more susceptible to the infection as the highest number of CFUs was detected in the kidneys of control animals and those treated with 25.0 or 50.0 mg/kg body weight of the compound. However, there was significant reduction in the number of CFUs in those animals which were treated with 100.0 to 400.0 mg/kg body weight of the purified antifungal compound 2-(3,4-dimethyl-2,5-dihydro-1H-pyrrol-2-yl)-1-methylethyl pentanoate (Table 3).

TABLE 3

COlony forming units in mice treated with various doses of the purified antifungal compound (2-(3,4-dimethyl-2,5-dihydro-1H-pyrrol-2-yl)-1-methylethyl pentanoate

| Groups | Dose (mg/kg body weight) | CFU/Organs (Mean + SD) | | |
|---|---|---|---|---|
| | | Lung | Liver | Kidney |
| I | 25.0 | 907.5 + 246.09 | 255.0 + 72.45 | 1402.5 + 350.09 |
| II | 50.0 | 900.0 + 230.29 | 290.6 + 135.58 | 1040.5 + 441.78 |
| III | 100.0 | 650.1 + 171.85 | 216.7 + 108.97 | 733.3 + 394.69 |
| IV | 200.0 | 525.0 + 251.56 | 225.0 + 91.85 | 683.3 + 352.67 |
| V | 400.0 | 180.0 + 127.75 | 165.0 + 117.84 | 225.0 + 157.39 |
| Control | 0.0 | 877.5 + 276.25 | 307.5 + 159.88 | 1440.0 + 439.89 |

The main advantages of the present invention are (i) Present invention provides a novel antifungal lead compound.

(ii) This novel molecule can be used to develop new drugs for treating various fungal diseases of humans.

(iii) Invention also provides a method for isolation, purification and characterisation of the novel antifungal compound from a plant *Datura metel.*

(iv) The novel molecule is less toxic than some of the available antifungal drugs in the market.

What is claimed is:

1. An antifungal compound 2-(3,4-dimethyl-2, 5-dihydro-1H-pyrrol-2-yl)-1-methylethyl pentanoate having the following formula:

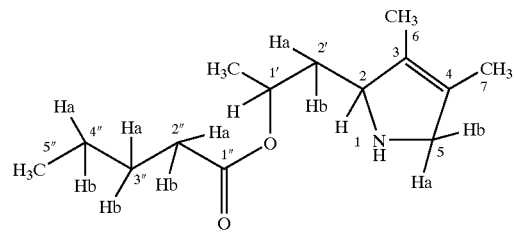

2. The antifungal compound of claim 1, wherein the said compound is characterized by known analytical methods selected from the group consisting of Thin Layer Chromatography (TLC), group specific chemical staining, UV, infrared, mass and nuclear magnetic resonance spectroscopy and biological assays selected from the group consisting of anti-mycotic assay and cytotoxicity assay and said molecule has following characteristics:

$R_f$ value of 0.22 on TLC,

Absorption maxima at 300 nm and 206 nm in UV spectrum,

IR $V_{Max:}$ 3434 (NH), 3024, 1711 (ester), 1646 (C≡C), 1524, 1426,1230, 938, 760 $cm^{-1}$, +ve FABMS m/z: 239 $[M]^+$ ($C_{14}$ $H_{25}$ $O_2$ N) (16.3), 212 (13.2), 174 (16.2), 122 (34.2), 102 (96.4), 58 (100), and 57 (19.2), 1H NMR ($CDCl_3$): δ 4.15 (1H, m, $C_{1'—H}$; 3.75 (1H, m, $C_{2'}$—H); 3.17 (2H, dd, J=7.44 Hz, 7.44 Hz, $C_5$—$H_a$ and $C_5$—$H_a$ and $C_5$—$H_b$); 2.31 (1H, t, J=6i.48 Hz, $C_{2''}$—$H_a$); 1.95 (1H, m, $C_{2''—Hb}$); 1.62 (6H, br, $C_6$—$CH_3$ and $C_7$—$CH_3$); 1.42 (1H, d, J=6.96 Hz, $C_{2'}$—$H_a$); 1.35 (1H, d, J=7.28 Hz, $C_{2'}$—$H_b$); 1.25 (7H, br, $C_{1''}$—$CH_{3''}$, $C_{3''}$—$H_b$ $C_{4''}$—$H_a$ and $C_{4''}$—$H_b$); 0.87 (3H, t, J=5.96 Hz, $C_{5''}$—$CH_3$) and COSY spectrum.

3. The antifungal compound as claimed in claim 1, wherein the $CT_{50}$ value of the compound is 889.2 μg/ml.

4. The antifungal compound as claimed in claim 1, wherein $ED_{50}$ for the compound is 167.0 mg/kg body weight.

5. The antifungal compound as claimed in claim 1, wherein cytotoxicity of said compound is 57.8 times less than Amphotericin B.

6. The antifungal compound as claimed in claim 1, wherein the compound is an antifungal agent.

7. A pharmaceutical composition, said composition comprising an effective amount of an antifungal compound 2-(3,4-dimethyl-2,5-dihydro-1H-pyrrol-2-yl)-1-methylethyl pentanoate along with pharmaceutically acceptable additives or adjuvants.

8. The composition as claimed in claim 7, wherein additives are selected from the group consisting of carbohydrate, protein, sugar and pharmaceutically acceptable carriers.

9. The composition as claimed in claim 7, wherein the effective dose of the antifungal compound is in the range of 100 to 400 mg/kg body weight.

10. The composition as claimed in claim 7, wherein said composition may be administered orally, intraperitoreal or by any other suitable routes.

11. The composition as claimed in claim 7, wherein the said composition is administered in the form of tablet, capsule, syrup, powder, ointment or injection.

12. The composition as claimed in claim 7, wherein the cytotoxicity of the said composition is 57.8 times less than Amphotericin B.

13. The composition as claimed in claim 7, wherein the said composition may be administered to subjects selected from mammals or humans.

14. A process for isolation of a novel antifungal molecule as claimed in claim 1, said process comprises the steps of:
  (i) extracting successively the powdered *Datura metel* plant material with an organic solvent at a temperature in the range of 15 to 45° C.,
  (ii) removing the solvent to obtain residue,
  (iii) extracting the above said residue obtained in step (ii) with an aliphatic hydrocarbon solvent followed by extraction with chloroform,
  (iv) removing chloroform from chloroform fractions,
  (v) screening the above obtained residue from chloroform fractions for antimycotic activity,
  (vi) separating the antifungal fractions and purifying the novel antifungal lead molecule from active antimycotic chloroform fractions by conventional chromatographic methods, and
  (vii) assaying the lead molecule obtained in step (vi) for antifungal acitivity and its cytotoxicity.

15. A process as claimed in claim 14, wherein in step (i) the solvent used for extraction is selected from methanol, ethanol, acetone, and chloroform.

16. A process as claimed in claim 14, wherein in step (ii) the purification of compound is carried out by column or thin layer chromatography (TLC) and high performance liquid chromatography (HPLC).

17. A process as claimed in claim 14, wherein in step (v) the aliphatic hydrocarbon solvent used is selected from pentane, hexane, petroleum ether and heptane.

18. A process as claimed in claim 14, wherein in step (vi) the purification of novel compound is carried out by Thin Layer Chromatography using solvent systems selected from Chloroform: Acetone: Diethylamine (5.0:4.0:1.0), Chloroform: Methanol: Diethylamine (8.5:1.5:0.1) and Chloroform: Methanol: Formic acid (8.0:2.0:0.1) or different combinations of above said organic solvents.

19. A process as claimed in claims 14, wherein in step (vi) the purification of novel compound is effected by HPLC using solvent system 70:30 of acetonitrile and water using reverse phase RP-8 column.

20. A process as claimed in claim 14, wherein in step (vi), the pure compound exhibits potential antifungal activity.

* * * * *